United States Patent
Kustermans et al.

(10) Patent No.: US 10,689,269 B2
(45) Date of Patent: Jun. 23, 2020

(54) FLUID TREATMENT SYSTEM

(71) Applicant: TROJAN TECHNOLOGIES, London (CA)

(72) Inventors: Mark Adrian Kustermans, Strathroy (CA); Michael Sasges, Victoria (CA); Robert Rennie, London (CA)

(73) Assignee: TROJAN TECHNOLOGIES, London, ON (CA)

( * ) Notice: Subject to any disclaimer, the term of this patent is extended or adjusted under 35 U.S.C. 154(b) by 0 days.

(21) Appl. No.: 16/061,033

(22) PCT Filed: Dec. 12, 2016

(86) PCT No.: PCT/CA2016/051456
§ 371 (c)(1),
(2) Date: Jun. 11, 2018

(87) PCT Pub. No.: WO2017/096490
PCT Pub. Date: Jun. 15, 2017

(65) Prior Publication Data
US 2018/0362368 A1      Dec. 20, 2018

Related U.S. Application Data

(60) Provisional application No. 62/386,759, filed on Dec. 11, 2015.

(51) Int. Cl.
*C02F 1/32*      (2006.01)
*A61L 2/10*      (2006.01)

(52) U.S. Cl.
CPC ............ *C02F 1/325* (2013.01); *A61L 2/10* (2013.01); *C02F 2201/3222* (2013.01);
(Continued)

(58) Field of Classification Search
CPC .. C02F 1/32; C02F 1/325; C02F 1/322; C02F 1/3221; C02F 1/3222; C02F 1/3227
(Continued)

(56) References Cited

U.S. PATENT DOCUMENTS 3,700,406 A * 10/1972 Landry .................... A61L 2/10
                                                        422/24
3,814,680 A    6/1974 Wood
(Continued)

FOREIGN PATENT DOCUMENTS

WO          95/13853        5/1995

OTHER PUBLICATIONS

International Search Report & Written Opinion, dated Mar. 8, 2017, pp. 7.
(Continued)

*Primary Examiner* — Jason L McCormack
(74) *Attorney, Agent, or Firm* — Ference & Associates LLC

(57) ABSTRACT

There is described a novel fluid treatment device that can induce Dean Vortices in the flowing fluid, and then induce a new set of Dean Vortices at an angle to those in the first set. Each subsequent curved section can induce vortices at an angle to those in the last curved section. This reactor has the effect of repeatedly twisting and splitting the fluid flow, resulting in targeted mixing similar to that of static mixers without the necessity of utilizing physical mixers. This is also an improvement over helical tubing configurations that generate only a single set of vortices and do not split and mix the flow.

11 Claims, 16 Drawing Sheets

(52) U.S. Cl.
CPC ............. *C02F 2201/3223* (2013.01); *C02F 2201/3227* (2013.01); *C02F 2301/024* (2013.01); *C02F 2301/026* (2013.01); *C02F 2301/028* (2013.01); *C02F 2303/04* (2013.01)

(58) Field of Classification Search
USPC .................. 250/437, 432 R, 455.11, 453.11
See application file for complete search history.

(56) References Cited

U.S. PATENT DOCUMENTS

| | | | |
|---|---|---|---|
| 4,422,773 A | | 12/1983 | Cassaday et al. |
| 4,769,131 A | | 9/1988 | Noll et al. |
| 6,150,663 A | * | 11/2000 | Rosenthal ............... A23L 2/50 250/435 |
| 2009/0084734 A1 | * | 4/2009 | Yencho .................. C02F 1/325 210/741 |
| 2010/0237254 A1 | | 9/2010 | Mason et al. |
| 2012/0241644 A1 | * | 9/2012 | Ben-David ............ C02F 1/325 250/436 |

OTHER PUBLICATIONS

European Patent Office, Communication pursuant to Article 94(3) EPC, dated Oct. 5, 2018, pp. 7.

\* cited by examiner

FLUID TREATMENT SYSTEM

CROSS-REFERENCE TO RELATED APPLICATION

The present application claims the benefit under 35 U.S.C. § 119(e) of provisional patent application Ser. No. 62/386,759, filed Dec. 11, 2015, the contents of which are hereby incorporated by reference.

BACKGROUND OF THE INVENTION

Field of the Invention

The present invention relates to a fluid treatment system. In another of its aspects, the present invention relates to a fluid mixing apparatus. In another of its aspects the present invention relates to a radiation source assembly that can irradiate the fluid mixing apparatus.

Description of the Prior Art

Fluid treatment systems are generally known in the art. Ultraviolet radiation is commonly used to disinfect fluids. UV inactivation has numerous advantages over other methods, including low operating costs and the elimination of chemicals.

For relatively clear fluids, simple systems employing ultraviolet light can be used to inactivate organisms in the fluid. For example, U.S. Pat. No. 4,482,809 describes a simple array of UV lamps that may be immersed in a flowing liquid, and is ideally suited to treating drinking water or relatively clear wastewater.

For fluids with higher optical absorbance of UV radiation, very thin fluid layers may be used. For example, Baroin patented a device (FR1101958) employing an annular thin film of fluid with thickness "between 1.5 and 2 mm" (See FIG. 1). More complicated systems have been used to produce a thin film through centrifugal force, as in GB191007669. Thin-film systems have the inherent disadvantage caused by the nearly-stagnant flow in the boundary layer. This can result in highly over-treated fluid near the radiation source, and under-exposed fluid in the distant boundary layer.

Another approach to treating strongly absorbing fluids is to induce mixing in the fluid in an attempt to ensure that all fluid elements are exposed to the UV radiation. U.S. Pat. No. 6,916,452 (Sure Pure) uses an annular flow path but attempts to induce swirling motion through a combination of the angle at which the fluid enters the annulus and a spiral groove in the outer wall of the reactor. FIG. 2. A more complex approach is taken in U.S. Pat. No. 7,695,675 (Bayer) that claims both active, powered mixers and mixing based on fluid instability.

The system in U.S. Pat. No. 7,695,675 also claims a method to overcome the mixing problem by arranging a fluid conduit in a helical path around a central lamp. Similar designs can be found in U.S. Pat. Nos. 5,069,782 and 5,150,705. Fluid flowing in this helical pathway can develop counter-rotating Dean Vortices that are intended to mix the fluid. However, the conduit has only a single curvature (the helix has only a single direction and pitch), so that the Dean Vortices, once formed, remain constant. An example is shown in FIG. 3. Fluid at the center of the vortices will remain in the center, while the fluid at the edge of the vortices will rotate around these central elements. As a result, there is a stratification of doses rather than the intended mixing.

Others, as in U.S. Pat. Nos. 3,814,680 and 8,653,481, have arranged UV-transparent tubular fluid conduits around a central lamp, but with the tubing arranged in a primarily axial direction, with bends to redirect the fluid back along the opposite direction. Since alternate bent sections are at approximately 180° to each other, any resulting vortices are in opposite direction, but the peripheral and core areas are not changed. This system has the same drawback of stratified dose described above.

Still another approach is described in U.S. Pat. Nos. 4,769,131 and 4,968,437. Here the inventors claim two UV-irradiated flow conduits "helically coiled in a paired manner", incorporating a filter element between the two conduits. See FIG. 4. A configuration that is described, but not claimed, shows two serpentine paths, each wrapping half-way around a central lamp, again with a filter element between the two paths. While this design incorporates a non-zero curvature as shown in Prior Art 3-B, which could induce vortexes, the subsequent reversal of direction shown in Prior Art 3-C has zero radius, and will not induce vortices.

Static mixers are a well-known and effective way to ensure good mixing in a fluid flow. These systems function by splitting the upstream flow into two or more paths and then rotating or twisting these paths. This process is repeated with subsequent mixers placed at an angle, typically 90° to the first, so that the fluid is repeatedly split and rotated. This approach is described in U.S. Pat. No. 6,586,172 (Iatros). Static mixers have the drawback that they act as an obstruction in the fluid flow and may become fouled with constituents of the flow. They also block the penetration of UV into the fluid conduit, which is a particularly important issue for strongly absorbing fluids.

It would be desirable to have a UV-based fluid treatment device for opaque fluids that would achieve the targeted dividing and rotating of the static-mixer systems without the drawbacks of these designs.

SUMMARY OF THE INVENTION

It is an object of the present invention to obviate or mitigate at least one of the above-mentioned disadvantages of the prior art.

It is another object of the present invention to provide a novel fluid treatment device suitable for UV-treatment of opaque fluid.

It is another object of the present invention to provide a novel method of treating fluid with ultraviolet radiation.

The method and device can be used to treat biological fluids and liquid foods including, but not limited to, whole blood and blood products including plasma, serum, vaccines, antibody solutions, cell culture media and constituents thereof, fermentation media, milk and milk products including whey, fruit juices, wine, cider and other liquids with strong absorbance or scattering of UV radiation.

In general, the method comprises the steps of irradiating a fluid with UV radiation between 200 nm and 400 nm while flowing the fluid in a fluid conduit that is at least partially transparent to said radiation, where the conduit has a section that is curved about a first axis, and a second section that is curved about a second axis that is not parallel to the first axis. Most preferably, these axes are at 90° to each other. Ideally, additional sections are included, each with an axis of curvature that is not parallel to that of the previous section. As a result of the fluid flowing in these curved sections, vortex motion may be induced in each curved section, and that motion is about an axis that is not parallel, and is nearly orthogonal to, the previous axis in the previous section. This has the result of repeatedly splitting and rotating the fluid so that it is well mixed and all the fluid receives the same amount of UV radiation.

Furthermore, since the fluid conduit does not wrap repeatedly around a central axis of symmetry, the UV source may be placed at one axis of curvature and the conduit does not necessarily enclose the DV source. This allows the conduit to be removed in a direction perpendicular to said axis, rather than along the axis. This minimizes the required axial length required for replacement of the conduit or lamp, eliminating a shortcoming of the helical arrangement proposed by others.

Thus the present inventors have conceived of a novel fluid treatment device that can induce Dean Vortices in the flowing fluid, and then induce a new set of Dean Vortices at an angle to those in the first set. Each subsequent curved section can induce vortices at an angle to those in the last curved section. This reactor has the effect of repeatedly twisting and splitting the fluid flow, resulting in targeted mixing similar to that of static mixers without the necessity of utilizing physical mixers. This is also an improvement over helical tubing configurations that generate only a single set of vortices and do not split and mix the flow.

BRIEF DESCRIPTION OF THE DRAWINGS

Embodiments of the present invention will be described with reference to the accompanying drawings, wherein like reference numerals denote like parts

FIG. 2B shows a detail of the same prior art system, with the inlet denoted 18. FIG. 2C provides a detail of the orientation of the inlet and outlet, intended to induce swirl in the incoming fluid consistent with the spiral fluid conduit. This design has the effect of causing the flowing liquid to take on a helical path that induces counter-rotating vortices.

DETAILED DESCRIPTION OF THE PREFERRED EMBODIMENTS

Figure 1:
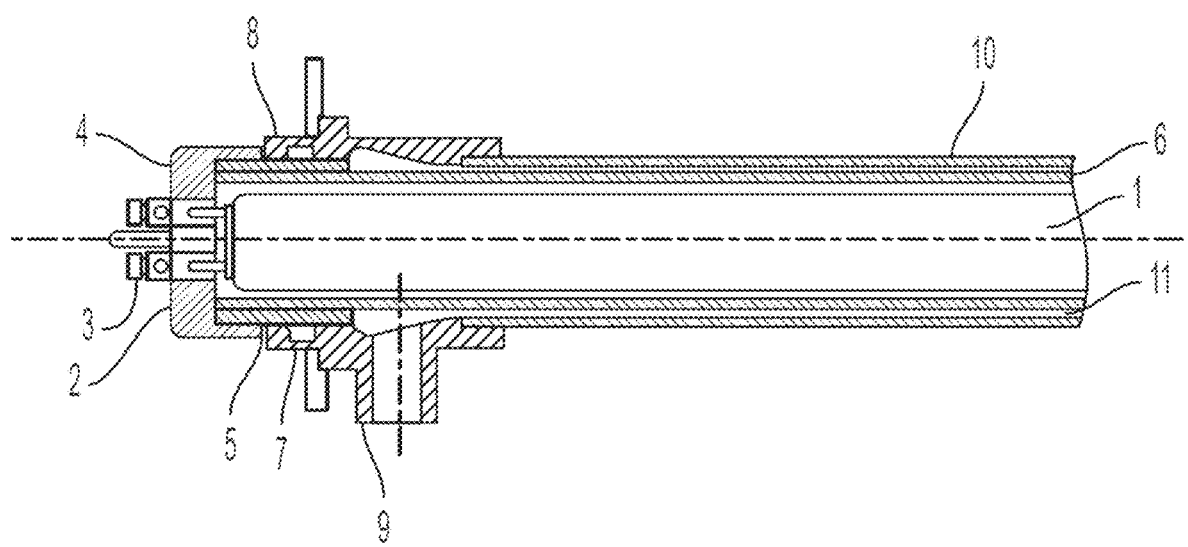
FIG. 1 illustrates a thin-film annular reactor design from FR1101958 (prior art).
Figure 2:
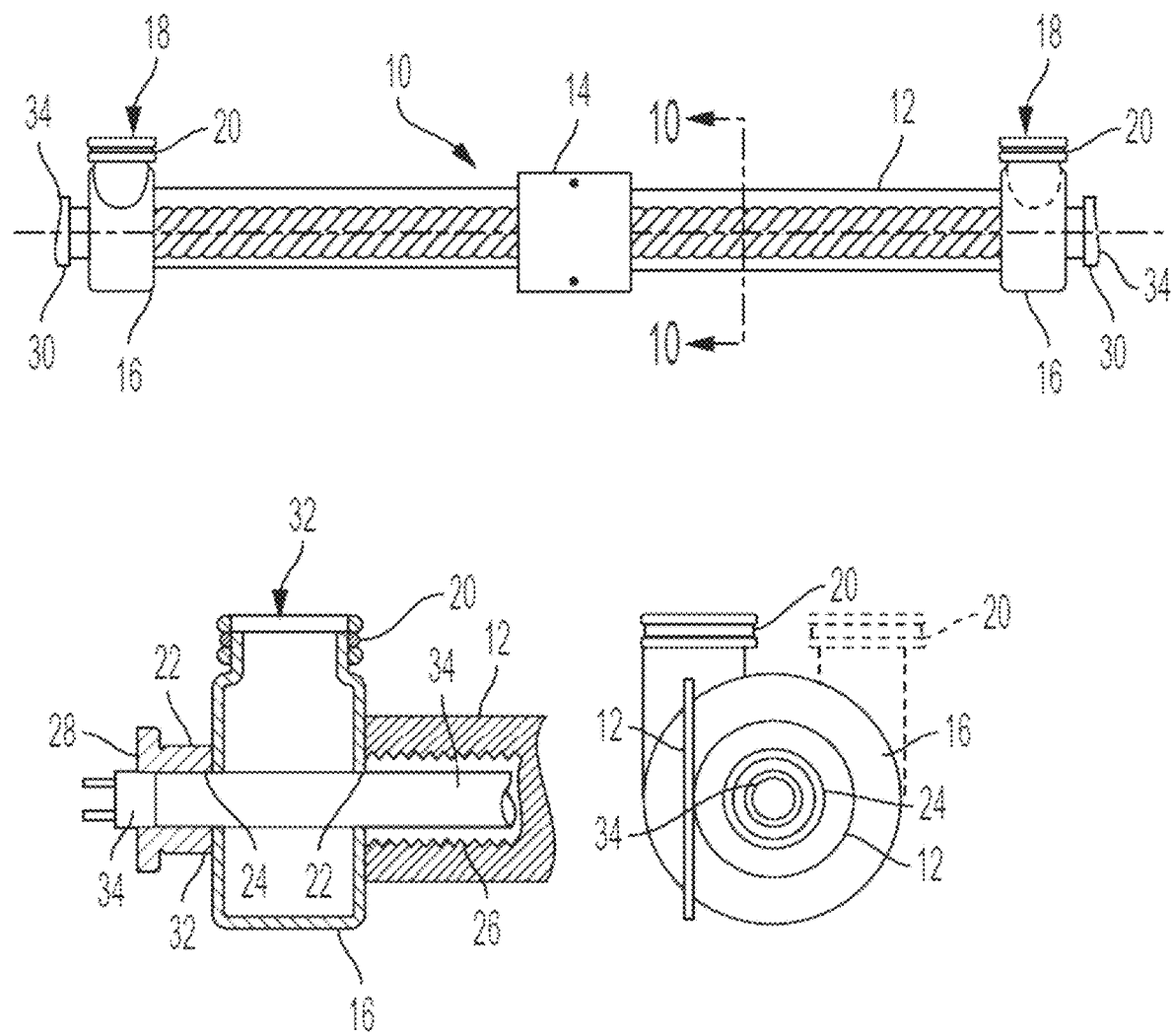
FIG. 2 illustrates a prior art fluid treatment device, in which an annular fluid conduit is formed with fluted sides and offset inlet and outlet segments, in order to induce helical flow in the fluid.
Figure 3:
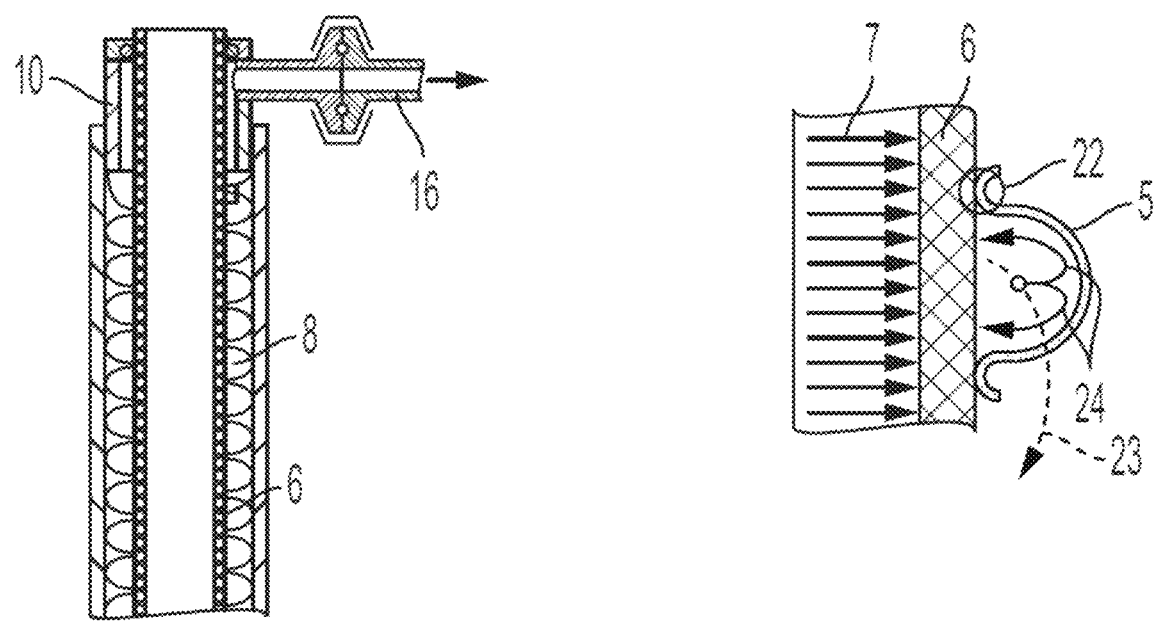
FIG. 3 shows prior art from U.S. Pat. No. 7,420,183 in which a helical flow path is formed between a transparent tube (6) and an outer fluted boundary, (5). There is only a single curvature radius and a single curvature axis
Figure 4:
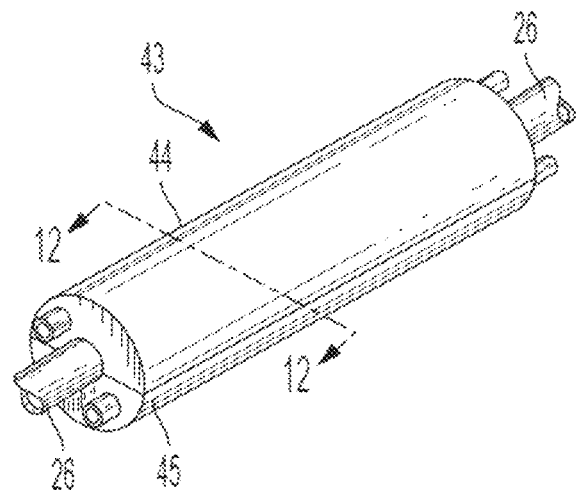
FIG. 4 represents prior art from U.S. Pat. No. 4,769,131 which does not use a tubular conduit and does not include alternating, non-zero radii of curvature for the fluid path. The square cross-section of the flow path is a hindrance to the formation of vortices, and the sharp, zero-radius curvature of the return portions will not induce vortices.
Figure 4:
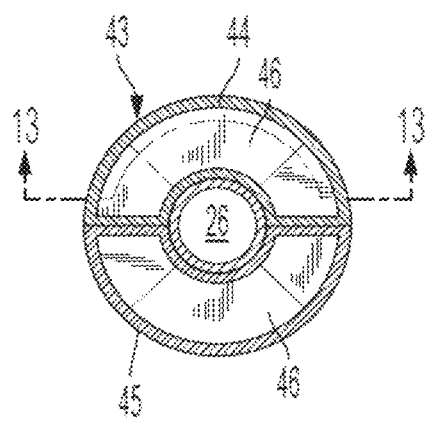
Figure 4:
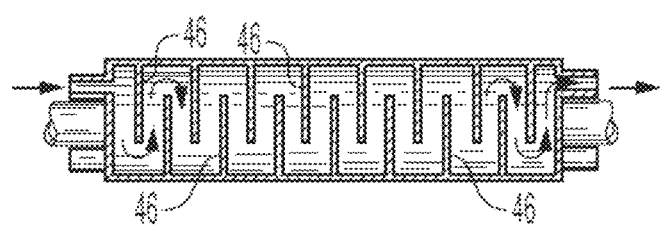
Figure 5:
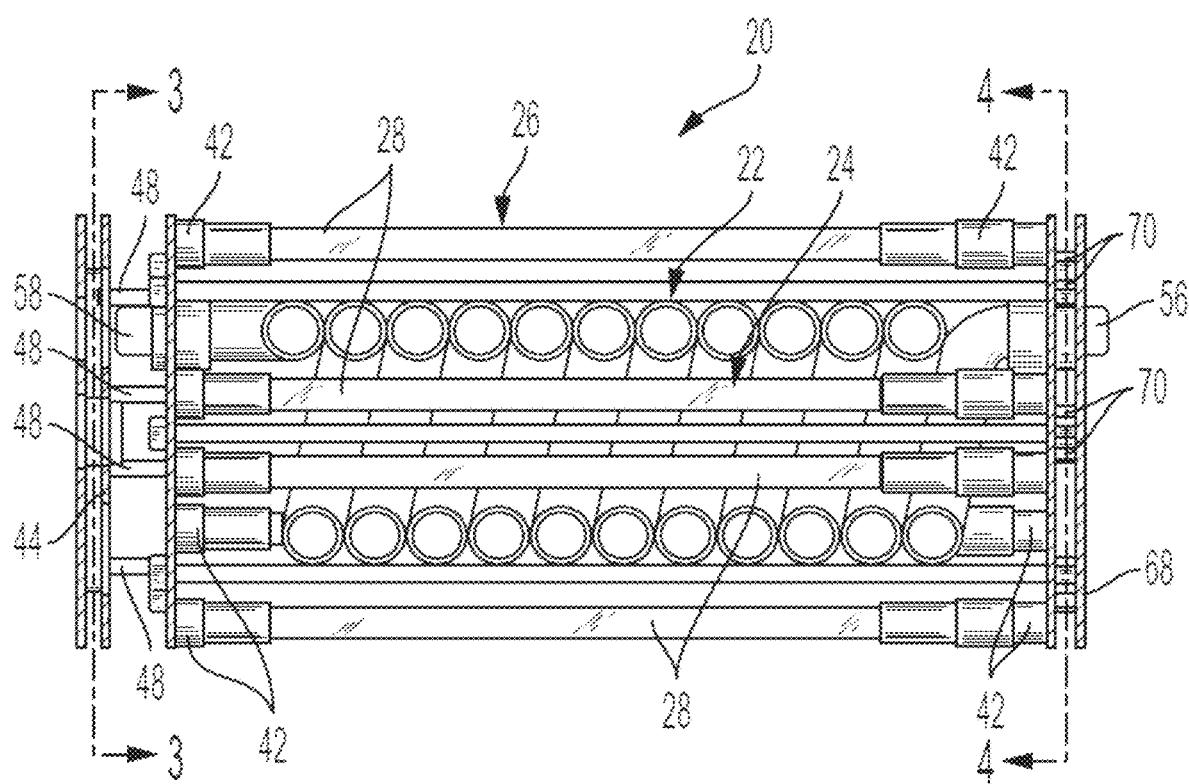
FIG. 5 represents prior art from U.S. Pat. No. 4,798,702, which arranges a UV-transmissive flow-conduit into a helical shape among several UV-emitting lamps.

Accordingly, in one of its aspects, the present invention provides a device for fluid treatment, comprising, a radiation source assembly, and a tubular fluid conduit that is at least partially transparent to radiation from the source assembly, wherein the fluid conduit is configured to have at least two curved sections, wherein each curved section is in a plane, and the planes are at an angle to one another.

Accordingly, in another of its aspects, the present invention provides a device for fluid treatment, comprising a radiation source assembly, and a tubular fluid conduit that is at least partially transparent to radiation from the source assembly, wherein the fluid conduit is configured to have two or more curved sections, wherein each curved section is in a plane, and each plane is at an angle to the adjacent plane or planes.

Accordingly, in another of its aspects, the present invention provides a device for fluid treatment, comprising a radiation source assembly, and a tubular fluid conduit that is at least partially transparent to radiation from the source assembly, wherein the fluid conduit is configured to have alternating curvatures, wherein each curved section is in a plane, and the planes are at an angle to one another.

Preferred embodiments of these devives may include any one or a combination of any two or more of any of the following features:
- adjacent planes form an angle of 60 degrees to 120 degrees;
- adjacent planes form an angle of 80 degrees to 100 degrees;
- adjacent planes are substantially orthogonal;
- there are at least two curvatures in the fluid conduit;
- the radii of curvature are the same;
- the radii of curvature are not all the same;
- the tubular conduit is circular in cross section;
- the conduit is non-circular conduit;
- the radiation source assembly emits in the wavelength range from 200 nm to 400 nm;
- the radiation source assembly comprises a mercury-vapor lamp;
- the radiation source assembly comprises Light Emitting Diodes; and/or
- the radiation source assembly has power consumption between 5 watts and 500 watts.

Accordingly, in yet another of it aspects the present invention provides a device for fluid treatment, comprising a radiation source assembly, and a tubular fluid conduit that is at least partially transparent to radiation from the source assembly, wherein the fluid conduit is configured to traverse the radiation source assembly in both the axial an lateral directions, wherein the direction of fluid flow with respect to the axis of the radiation source assembly is reversed one or more times. Preferred embodiments of these devives may include any one or a combination of any two or more of any of the following features:
- the fluid conduit has two or more curved sections, wherein each curved section is in a plane, and each plane is at an angle to the adjacent plane or planes;
- the fluid conduit is configured to have alternating curvatures, wherein each curved section is in a plane, and the planes are at an angle to one another;
- adjacent planes form an angle of 60 degrees to 120 degrees;
- adjacent planes form an angle of 80 degrees to 100 degrees;
- adjacent planes are substantially orthogonal;
- there are at least two curvatures in the fluid conduit;
- the radii of curvature are the same;
- the radii of curvature are not all the same;
- the tubular conduit is circular in cross section;
- the conduit is non-circular conduit;
- the radiation source assembly emits in the wavelength range from 200 nm to 400 nm;
- the radiation source assembly comprises a mercury-vapor lamp;
- the radiation source assembly comprises Light Emitting Diodes; and/or
- the radiation source assembly has power consumption between 5 watts and 500 watts.

In a preferred embodiment, the system incorporates a central elongated mercury vapor lamp. It incorporates a fluid conduit constructed from tubing laid in a looping pattern that is also curved around the lamp axis, giving rise to two axes of curvature: one approximately aligned with the lamp axis, and the other perpendicular to the lamp axis.

The tubing can be made of a fluorinated material such as PTFE (polytetrafluoroethylene), FEP (Fluorinated Ethylene Propylene, for example Pharmafluor from St. Gobain), or THV (a polymer of tetrafluoroethylene, hexafluoropropylene and vinylidene fluoride). These materials are resistant to chemical attack, and are at least partially transparent to UV radiation.

Figure 6:
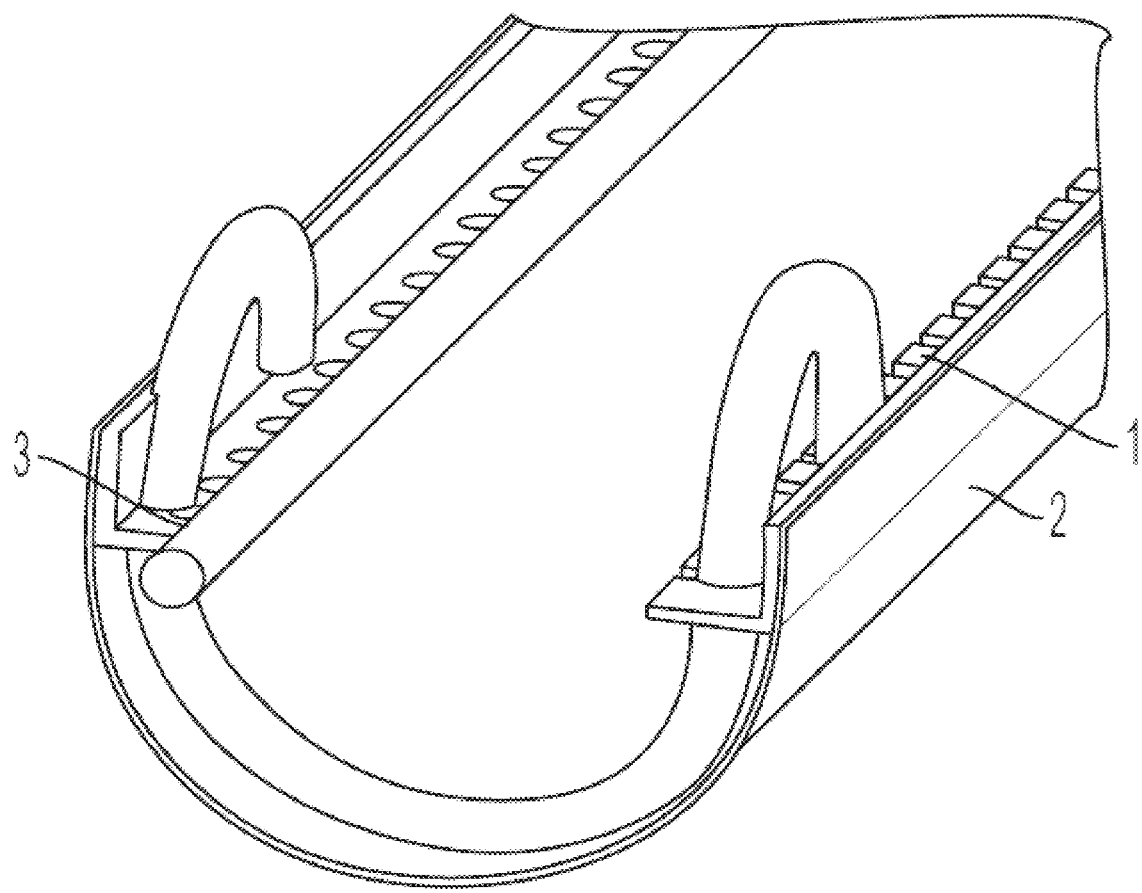
FIG. 6 illustrates a preferred embodiment of the present invention, with the fluid conduit arranged to achieve alternating curvatures. A UV emitter can be placed along the axis of curvature of one of these sections.

A simple way to achieve the desired arrangement is to lay the tubing in a coiled array along a flat surface, and then to press this coiled array into a curved shape. This configuration is shown in FIG. 6, which includes two sequential coiled arrays as described above.

The same feature of alternating curvatures could also be made with tubing laid in a back-and-forth pattern with ~270° return loops to bring the tubing back to the reverse direction. One curvature is in the return loop, the other curvature is in the section curved around the lamp.

The fluid conduit as described can be removed from the central lamp in a radial direction. This minimizes the space required for removing and replacing the fluid conduit or the lamp, which would otherwise require an axial length greater than two times the length of the lamp.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description.

Performance of a Preferred Embodiment of the Invention

A system has been constructed as described in this document and tested over a wide range of fluid flow rates and optical properties. UV fluence (dose) delivery was evaluated using phage (virus) inoculated into fluids of various optical absorbance (opacity). The surviving phage were cultured and counted after irradiation, and the log reduction in numbers used to calculate the Fluence.

Figure 7:
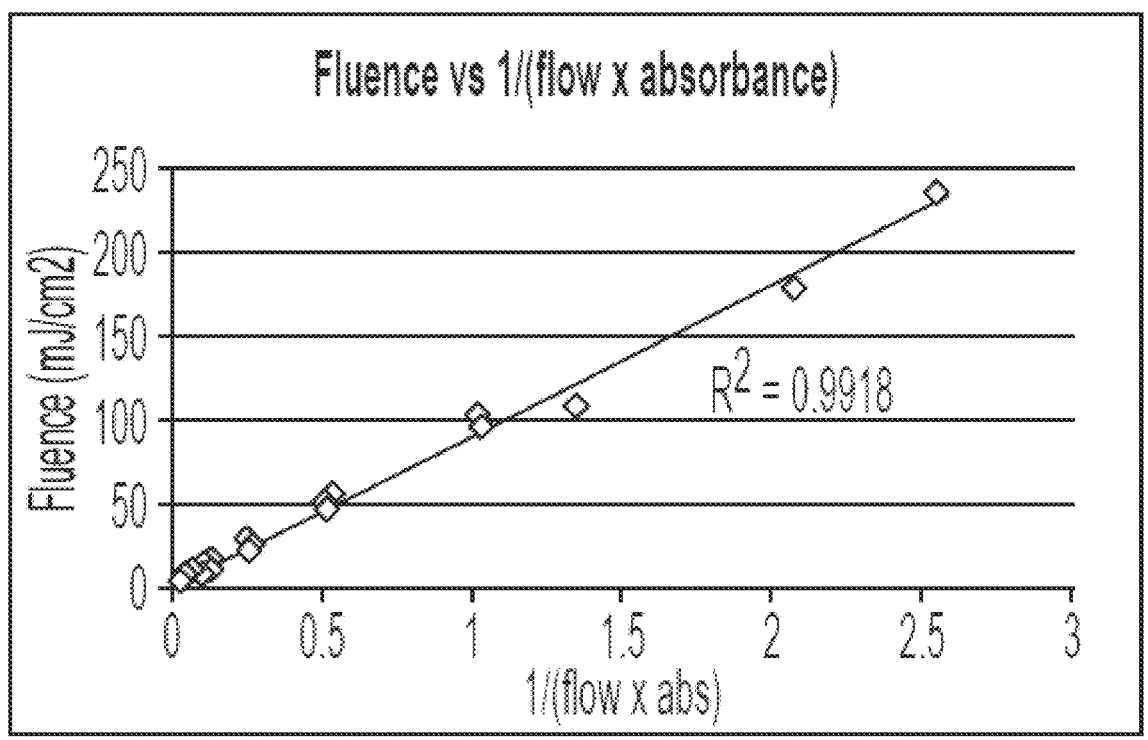
FIG. 7 depicts the performance of a preferred embodiment of the multi-pass reactor design over a wide range of fluid flow rates and optical properties.

It was found that the reactor behaved in an ideal fashion, with measured Fluence inversely proportional to flow rate and absorbance—see FIG. 7.

Figure 8:
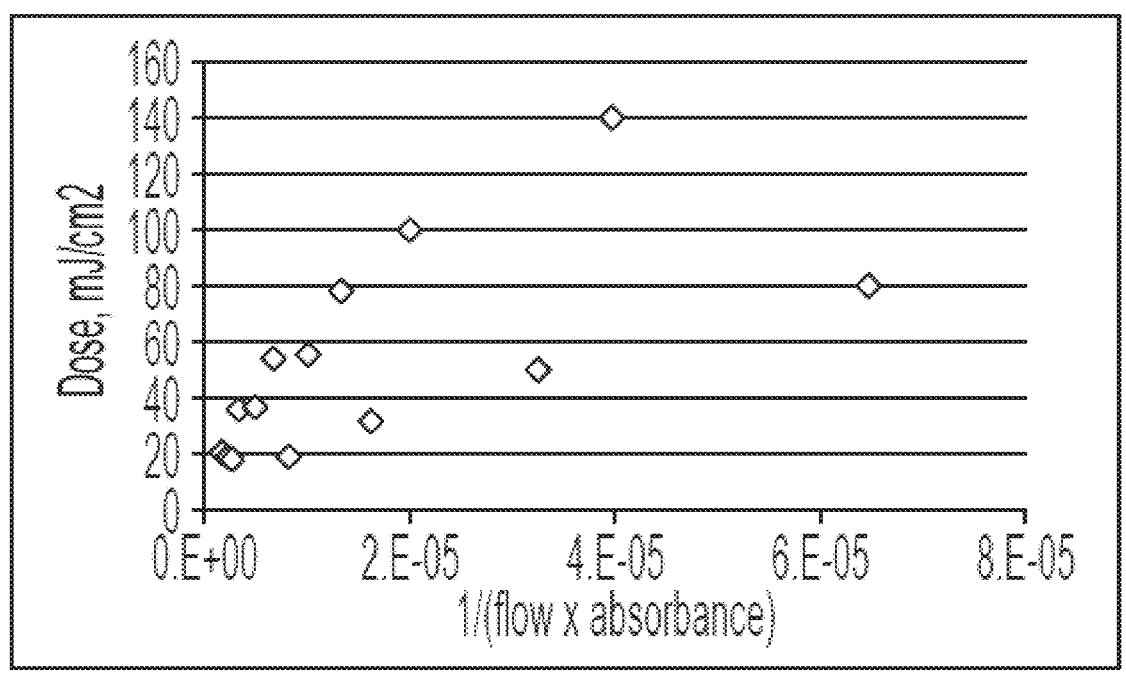
FIG. 8 depicts the performance of a very thin film reactor with a 1 mm water and built around the same lamp as that used in a preferred embodiment of the present fluid treatment device tested over a wide range of fluid flow rates and optical properties.

Thin film reactors are often used to treat strongly absorbing fluids, depending on the thin water layer to induce good mixing. A very thin film reactor, with a 1 mm annular flow layer, was built around the same lamp as that used in the inventive reactor. This reactor was tested using the same organisms and range of fluid optics used in the test of the inventive reactor, and the results are shown in the FIG. 8. In contrast to the inventive reactor, the data do not form a straight line in this plot, and do not even cluster on a single curve. This performance is poor, and indicates that good mixing was not attained.

Figure 9:
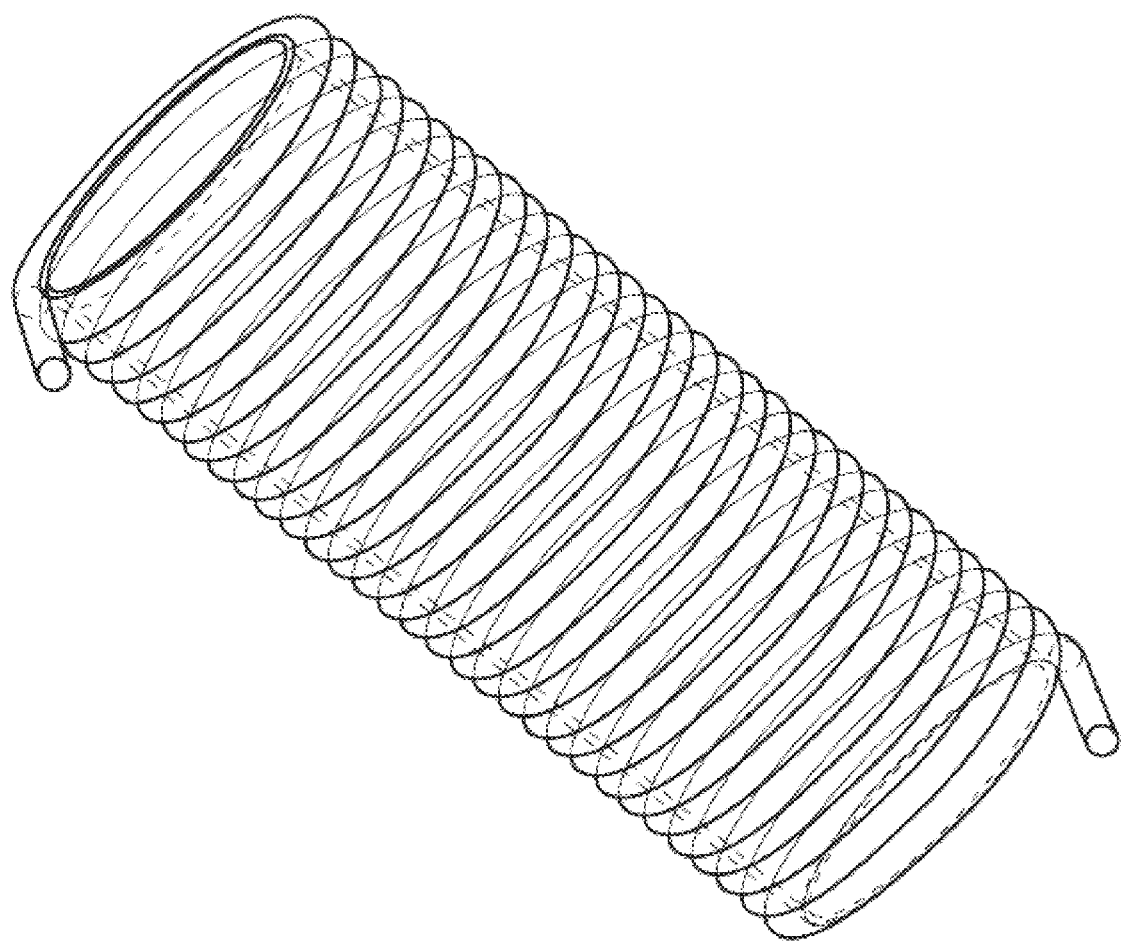
FIG. 9 illustrates a helical spiral reactor constructed for comparison with a preferred embodiment of the present fluid treatment device.

A helical spiral reactor was also constructed for comparison against the inventive reactor. The same lamp and power supply was used, and the same type and diameter of Teflon tubing was used to create a close-packed helical flow path around the central lamp, as taught by U.S. Pat. Nos. 7,695, 675, 5,069,782 and 5,150,705. A diagram of the reactor is shown in FIG. 9. Tests were conducted in the same manner as those for the other reactors, with challenge organisms being treated by pumping a test fluid of known absorbance through the helical flow path.

Figure 10:
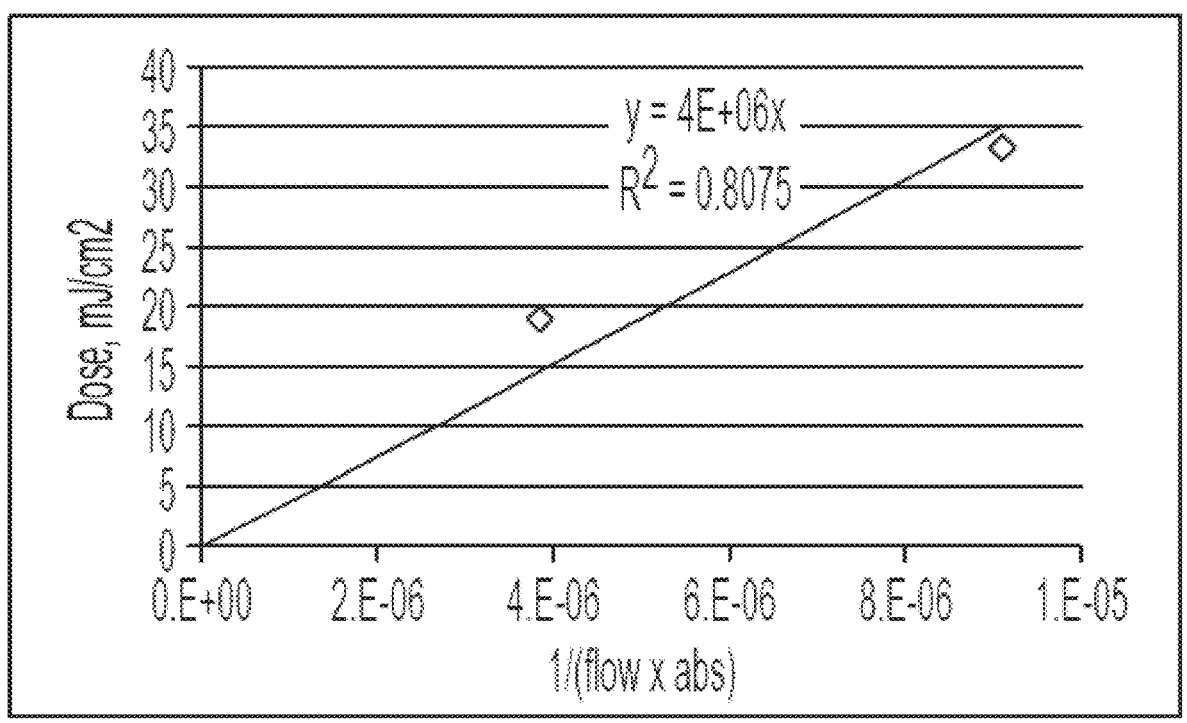
FIG. 10 shows the measured Fluence vs. 1/(Flow×Absorbance) for the Spiral (Helical) Reactor.

The results were plotted in similar manner and may be seen in FIG. 10. Clearly the performance of this reactor does not follow the same 1/flow behavior that is achieved by the inventive reactor. While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

Modeling

A variant of this reactor design, using a fluid conduit consisting of offset curved sections separated by straight sections, was modeled using Fluent CFD software. This software can simulate fluid flow by using the Navier-Stokes equations coupled with the continuity equations, and is used extensively in aerodynamic and other applications.

The simulated flow through the curved sections of the reactor resulted in counter-rotating vortices, as expected. The Fluent software has the capability to show the magnitude of "helicity", or rotational flow, corresponding to rotating vortices. This flow is represented schematically in FIG. 11, and the simulated flow is shown in the following figure. This figure shows that the curved sections of the fluid conduit result in positive and negative helicity, shown in white or dark color, respectively, corresponding to counter rotating vortices (Dean vortices).

Figure 11:
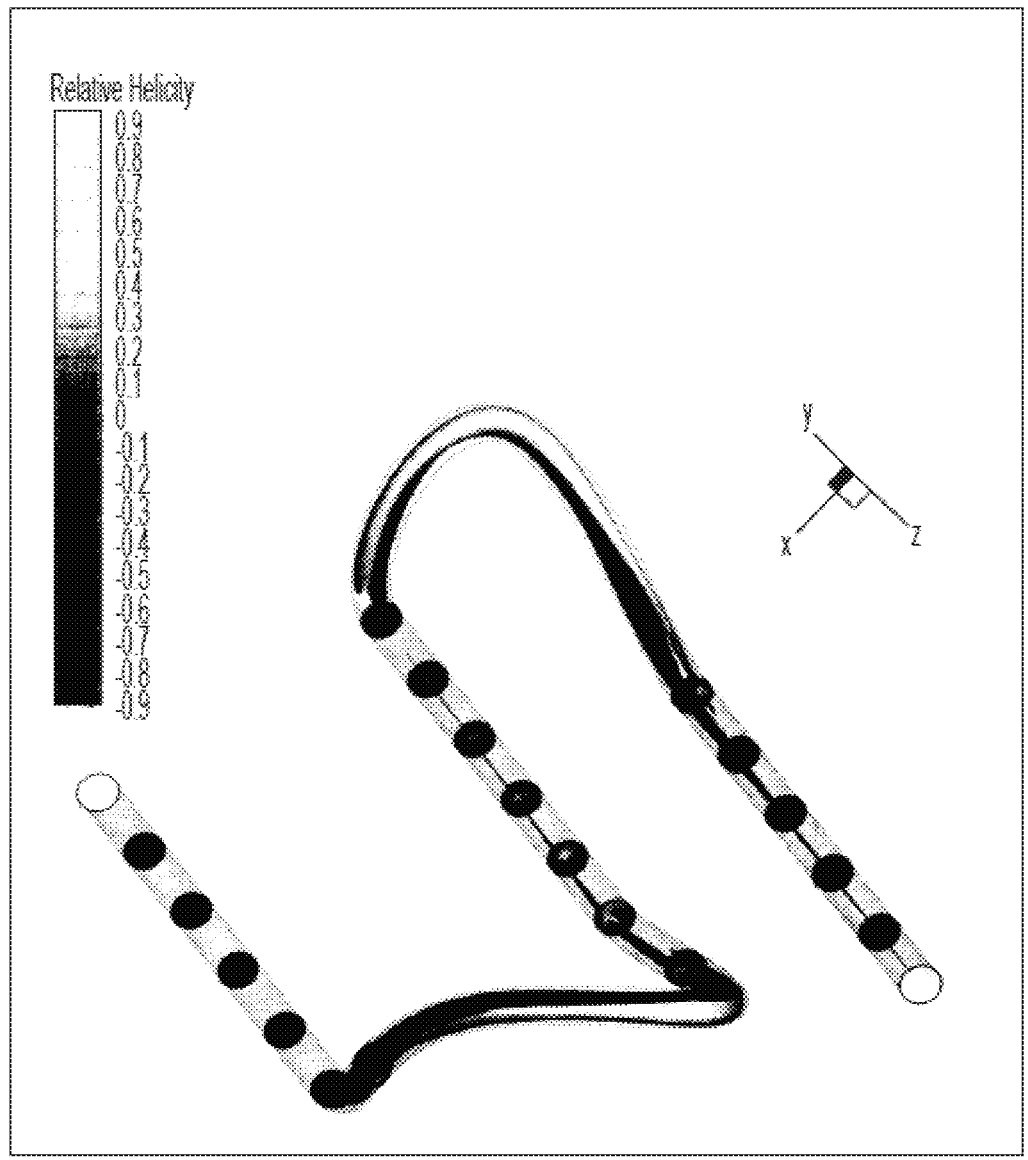
FIG. 11 is the computer generated fluid model of the fluid flow through curved section of the reactor.
Figure 12:
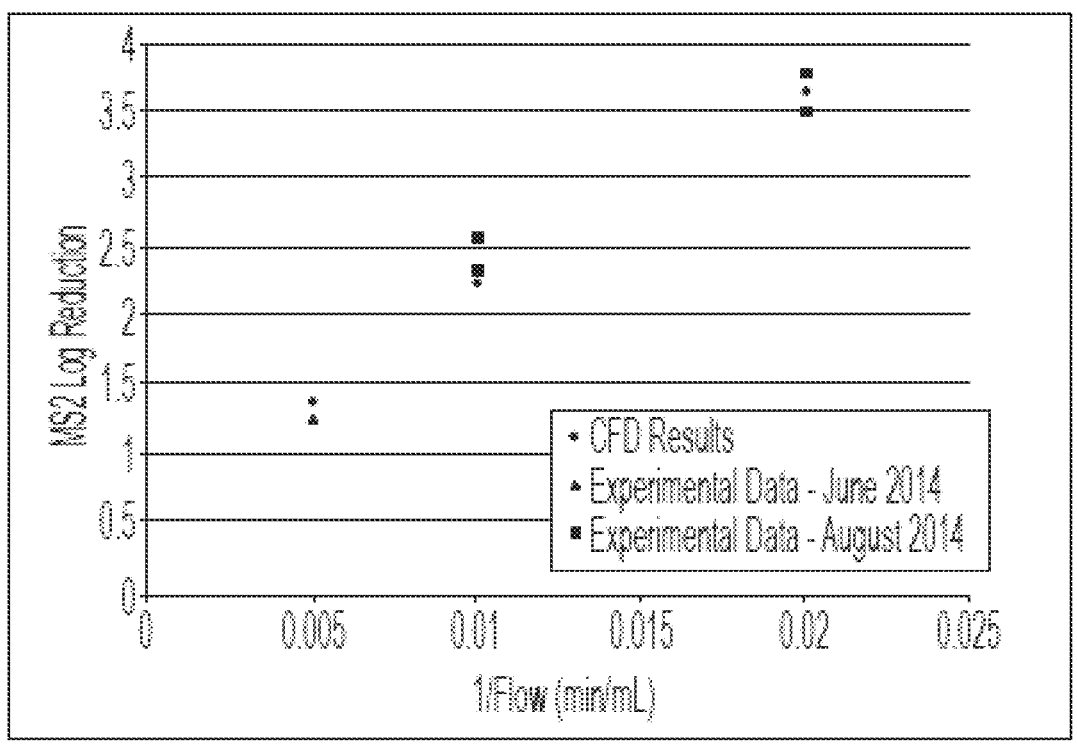
FIG. 12 illustrates compared the results of the CFD model to experimental results
Figure 13:
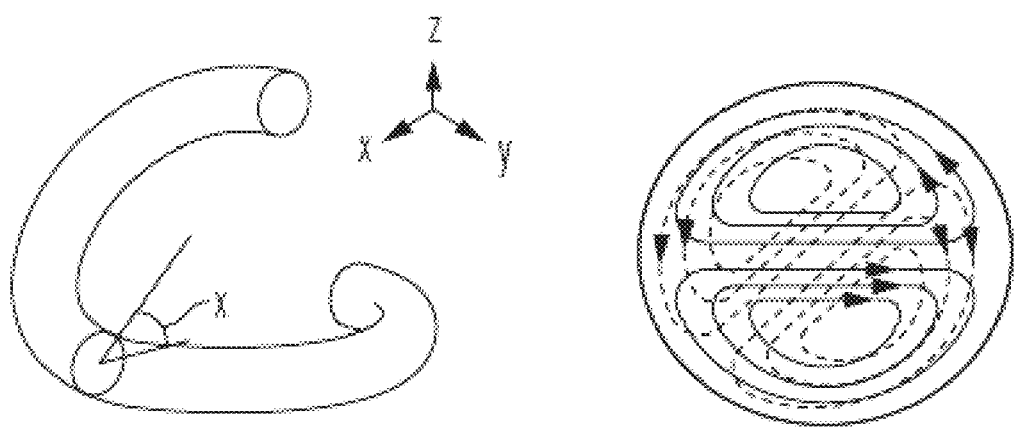
FIG. 13 illustrates how curved sections of conduit, arranged in sequence, can set up vortices that are offset. This work is by Jones et al. In that work, the authors state that the ideal configuration with alternating curvatures cannot be achieved in reality, as they had not conceived of the present invention. They do not include or consider a UV source, and their analysis does not consider disinfection.
Figure 14:
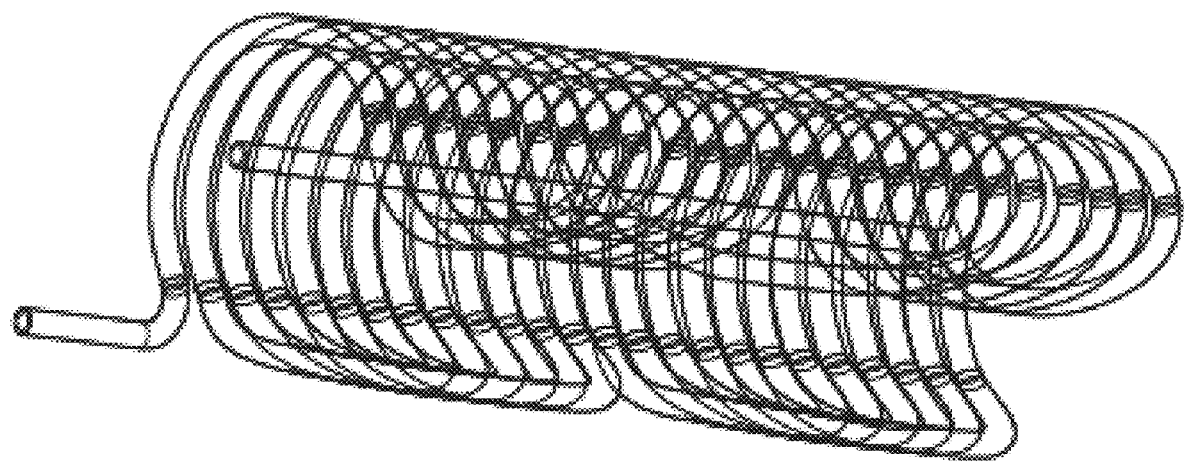
FIG. 14 shows a convenient way to implement this alternating curvature. The fluid enters the conduit at the upper right, then curves 90 degrees and then travels in a direction along a curved outer retainer before curving in a direction roughly parallel to the axis of curvature of the outer retainer before following the curved retainer back in the opposite direction from the first, before again curving in a direction roughly parallel to the axis of curvature of the outer retainer but in opposite direction to the first pass. In this way, the tubing forms a large loop back to a point near the starting point. The second large loop is shifted axially with respect to the first, and this pattern is continued until the tubing has covered most of the area of the outer retainer in this region. At that point, a new looping pattern may be formed that is shifted axially with respect to the first, as shown in FIG. 14. Each looping pattern can be formed by laying down a coil of tubing on a flat surface, then curving the flat surface into the retainer shape shown in FIG. 14.
Figure 15:
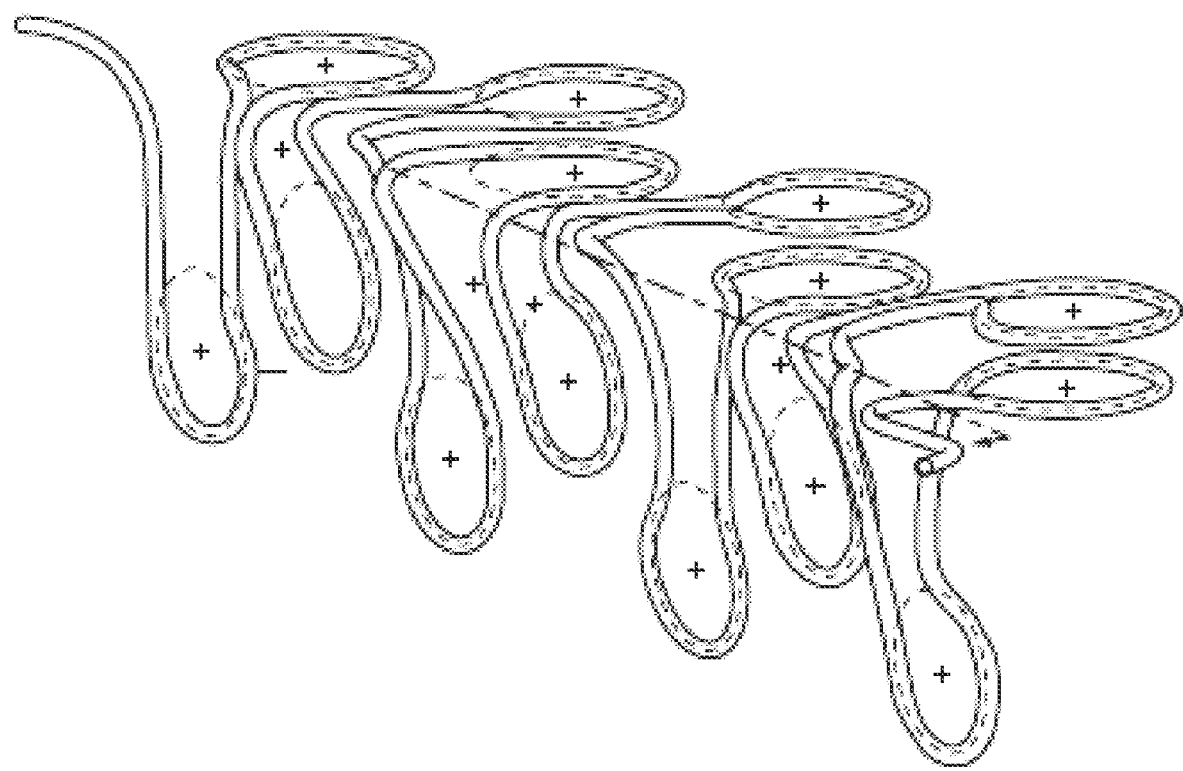
FIG. 15 shows an embodiment that is particularly well adapted to planar light sources, such as flat arrays of Light Emitting Diodes. In this case the conduit has alternating curvature in order to induce alternating vortexes, but these alternating curvatures are in two planes that are arranged at 90 degrees to each other. Planar arrays of LEDs or other planar light sources (not shown) can be provide in each plane, each irradiating one of the set of curved segments.
Figure 16:
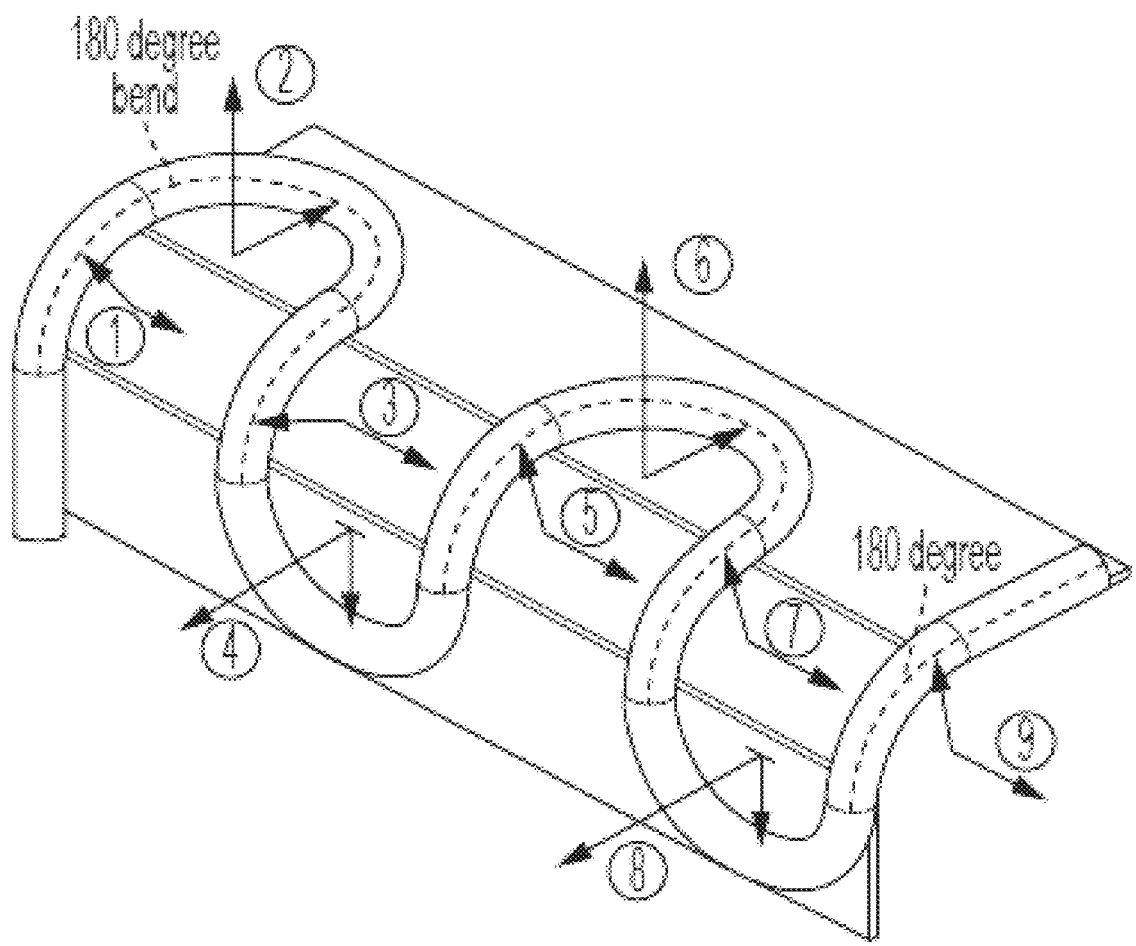
FIG. 16 shows an embodiment that has four curved sections in sequence, where the axes of the first and third section are parallel to each other, and orthogonal to the axes of the second and fourth sections. The axes of the second and fourth sections are orthogonal to each other. Sequential curved sections have axes of curvature that are orthogonal to each other: Curvature of the first section is orthogonal to that of the second; curvature of the second section is orthogonal to that of the third, etc

This reactor was also fabricated and used to inactivate MS2 phage (virus) so that the applied UV Dose could be measured. The measured results agreed very closely with the predictions from the CFD simulation, as are shown in FIG. 11

All publications, patents and patent applications referred to herein are incorporated by reference in their entirety to the same extent as if each individual publication, patent or patent application was specifically and individually indicated to be incorporated by reference in its entirety.

What is claimed is:

1. A device for fluid treatment, comprising
a radiation source assembly,
and a tubular fluid conduit that is at least partially transparent to radiation from the source assembly,
wherein the tubular fluid conduit is configured to have at least a first curved section and a second curved section sequentially adjacent to the first curved section,
wherein the first curved section and the second curved section are non-parallel sections,
wherein the first curved section and the second curved section alternate sequentially to form a non-helical shape of the tubular fluid conduit;
wherein the first curved section is in a first plane and the second curved section is in a second plane, and the first plane and the second plane are at an angle to one another.

2. The device defined in claim 1, wherein the first plane and the second plane form an angle of 60 degrees to 120 degrees.

3. The device defined in claim 1, wherein the first plane and the second plane form an angle of 80 degrees to 100 degrees.

4. The device defined in claim 1, wherein the first plane and the second plane are substantially orthogonal.

5. The device defined in claim 1, in which the first curved section comprises a first radius of curvature and the second curved section comprises a second radius of curvature.

6. The device defined in claim 5, in which the first radius of curvature and the second radius of curvature are the same.

7. The device defined in claim 1, wherein the tubular conduit is circular in cross section.

8. The device defined in claim 1, wherein the radiation source assembly emits in the wavelength range from 200 nm to 400 nm.

9. The device defined in claim 1, wherein the radiation source assembly comprises a mercury-vapor lamp.

10. The device defined in claim 1, wherein the radiation source assembly comprises Light Emitting Diodes.

11. The device defined in claim 1, wherein the radiation source assembly has a power consumption between 5 watts and 500 watts.

* * * * *